(12) United States Patent
Jain et al.

(10) Patent No.: US 9,783,479 B1
(45) Date of Patent: Oct. 10, 2017

(54) (METH)ACRYLIC ACID PRODUCTION PROCESS

(71) Applicant: Arkema France, Colombes (FR)

(72) Inventors: Sandeep Jain, Paris (FR); Christian Lacroix, Forbach (FR)

(73) Assignee: Arkema France, Colombes (FR)

( * ) Notice: Subject to any disclaimer, the term of this patent is extended or adjusted under 35 U.S.C. 154(b) by 0 days.

(21) Appl. No.: 15/452,757

(22) Filed: Mar. 8, 2017

(51) Int. Cl.
*C07C 51/25* (2006.01)
*C07C 51/44* (2006.01)
*C07C 51/42* (2006.01)

(52) U.S. Cl.
CPC .......... *C07C 51/252* (2013.01); *C07C 51/44* (2013.01)

(58) Field of Classification Search
CPC ................. C07C 51/44; C07C 51/42
See application file for complete search history.

(56) References Cited

U.S. PATENT DOCUMENTS 8,242,308 B2 * 8/2012 Ho .................. C07C 51/44
562/600

FOREIGN PATENT DOCUMENTS

| EP | 2 066 613 B3 | 6/2012 |
| WO | WO 2008/033687 A2 | 3/2008 |
| WO | WO 2016142608 A1 * | 9/2016 |

* cited by examiner

*Primary Examiner* — Paul A Zucker
(74) *Attorney, Agent, or Firm* — Lynn B. Morreale

(57) ABSTRACT

The invention relates to the production of (meth)acrylic acid, and to implementation of a step of condensing water contained in a recycled gas effluent and/or in the air feed in a (meth)acrylic acid production process, which further includes a process for purifying a reaction mixture comprising (meth)acrylic acid without using azeotropic solvent and based on the use of two distillation columns.

12 Claims, 3 Drawing Sheets

(METH)ACRYLIC ACID PRODUCTION PROCESS

CROSS-REFERENCE TO RELATED APPLICATIONS

This application claims priority under 35 U.S.C. §119 to French application FR16.52683, filed 29 Mar. 2016.

TECHNICAL FIELD

The present invention relates to the production of (meth) acrylic acid.

The subject thereof is more particularly the implementation of a step of condensing the water contained in a recycled gas effluent and/or in the air feed, in a (meth)acrylic acid production process which includes a process for purifying a reaction mixture comprising (meth)acrylic acid without using azeotropic solvent and based on the use of two distillation columns.

The process according to the invention makes it possible to reduce the (meth)acrylic acid losses during the purification, and overall to improve the efficiency of the process.

TECHNICAL BACKGROUND AND TECHNICAL PROBLEM

The acrylic acid synthesis process employed on a large industrial scale implements a reaction for catalytic oxidation of propylene in the presence of oxygen.

This reaction is generally carried out in the gas phase, and usually in two steps: the first step carries out the substantially quantitative oxidation of the propylene in an acrolein-rich mixture, and then, during the second step, the selective oxidation of the acrolein to acrylic acid is carried out.

The gas mixture resulting from the second step consists, other than of the acrylic acid:

of the impurities resulting from the first reaction step which have not reacted (propylene, propane);

of light compounds which are non-condensable under the temperature and pressure conditions normally used, and which are not converted in the first step or are formed in the second step: nitrogen, unconverted oxygen, carbon monoxide and dioxide formed in a small amount by final oxidation or going around in circles, by recycling, in the process;

of condensable light compounds which are not converted in the first step or are formed in the second step: water, unconverted acrolein, light aldehydes, such as formaldehyde and acetaldehyde, formic acid, acetic acid or propionic acid;

of heavy compounds: furfuraldehyde, benzaldehyde, maleic acid and anhydride, benzoic acid, 2-butenoic acid, phenol, protoanemonin.

The complexity of the gas mixture obtained in this process makes it necessary to carry out a set of operations in order to recover the acrylic acid contained in this gas effluent and to convert it into a grade of acrylic acid compatible with its final use, for example the synthesis of acrylic esters or the production of polymers of acrylic acid and/or of acrylic esters.

A new acrylic acid recovery/purification technique has recently emerged, involving a reduced number of purification steps and not requiring any external organic solvent.

Patent EP 2 066 613, based on this "solvent-free" technique, describes a process for recovering acrylic acid without using external water or azeotropic solvent and using only two columns for purifying the cooled gas reaction mixture: a) a dehydration column, b) and a finishing column (or purification column) fed with a part of the stream from the bottom of the dehydration column.

According to this process, the cooled gas reaction stream is subjected to dehydration in a first column. The gas stream distilled at the top of the column is sent to a condenser, in which the light compounds are partly condensed and sent back to the dehydration column in reflux form in order to absorb the acrylic acid, the gas effluent being at least partly sent back to the reaction and the remainder being incinerated.

The stream from the bottom of the dehydration column feeds a second column which makes it possible to separate, by drawing off from the side, in liquid or vapour form, a stream of purified acrylic acid corresponding to a technical grade. The technical-grade acrylic acid obtained generally has a purity greater than 98.5% by weight and contains less than 0.5% by weight of water.

In this finishing column, the top distillate comprising water and light by-products is condensed and then recycled to the bottom of the first column, and a stream comprising acrylic acid enriched with heavy by-products is eliminated at the bottom so as to optionally be used for the production of acrylic esters.

In this process, a part of the streams (from the bottom of the dehydration column or from the top of the finishing column) is advantageously sent back to the heating/reboiler devices of the dehydration column and/or used to cool the gas reaction mixture, thereby making it possible to optimize the energy requirements of the process.

Despite the advantages provided by the purification process described in document EP 2 066 613, there still remain drawbacks associated with its implementation, in particular in terms of the possible loss of acrylic acid during the various steps.

In particular, acrylic acid can be entrained at the top of the dehydration column. Depending on the liquid/vapour equilibrium at the operating temperature of the condenser placed at the top, the gas effluent at the outlet may contain acrylic acid in a not insignificant amount. Acrylic acid is directly lost in the part of the gas effluent that is incinerated.

There thus remains a need to reduce the acrylic acid losses in a solvent-free recovery/purification process based on the use of a dehydration column and of a finishing column, and in particular to reduce the acrylic acid losses at the top of the dehydration column.

The inventors have now discovered that the acrylic acid loss can be reduced by controlling the content of water introduced into this process.

The main source of water comes from the crude reaction mixture to be treated, since it contains the water formed during the reaction for catalytic oxidation of the propylene to acrylic acid. The water is the main "light" impurity that is distilled at the top of the dehydration column, and its elimination during the purification process conditions the quality that is sought for the purified acrylic acid (water content <0.5% by weight).

It is necessary to eliminate the water in an optimal manner at the top of the dehydration column while at the same time minimizing the acrylic acid loss. It is possible, for example, to reduce the temperature of the condenser placed at the top, so as to modify the liquid/vapour equilibrium and to prevent entrainment of acrylic acid in the gas effluent. However, this is possible only within a certain limit that depends on the water content introduced into the dehydration column.

In addition to the water inherent in the acrylic acid synthesis process, water is introduced by other routes, such as, for example, the moisture content present in the air stream introduced into the reaction in order to carry out the oxidation of the propylene. Moreover, aqueous solutions of polymerization inhibitors are introduced into the columns and/or condensers in order to limit the polymerization reactions, and the water thus introduced can go around in circles in the process by recycling and/or reflux.

It has been discovered that, by reducing these supplementary sources of water, the elimination of the water at the top of the dehydration column can be optimized, while at the same time minimizing the acrylic acid losses.

According to the invention, it is proposed to condense the water present in the air stream feeding the reaction, and/or the water present in the gas effluent from the dehydration column which is recycled to the reaction.

Moreover, it has become apparent to the inventors that this invention can be applied to the acrylic acid produced from sources other than propylene, to methacrylic acid, and also to these acids derived from renewable raw materials, which are capable of posing the same purification problems associated with the presence of water.

SUMMARY OF THE INVENTION

The present invention relates first and foremost to a (meth)acrylic acid production process, comprising at least the following steps:

i) at least one (meth)acrylic acid precursor is subjected to gas-phase oxidation in the presence of air so as to form a gas reaction mixture comprising (meth)acrylic acid;

ii) the gas reaction mixture is cooled;

iii) the gas reaction mixture is subjected to dehydration without using azeotropic solvent in a first column, termed dehydration column, resulting in a top gas stream and in a bottom stream;

iv) the gas stream distilled at the top of the dehydration column is at least partly subjected to condensation in a top condenser, the condensate being sent back to the dehydration column in reflux form in order to absorb the acrylic acid, and the gas effluent being at least partly sent back to the oxidation reaction and the remainder being subjected to thermal and/or catalytic oxidation;

v) the stream from the bottom of the dehydration column is at least partly subjected to distillation in a second column, termed finishing column, resulting in a top stream, and in a bottom stream containing heavy compounds;

vi) a (meth)acrylic acid stream is recovered by drawing off from the side of the finishing column;

said process being characterized in that a water condensation step applied to at least one of the following two streams is carried out: the air feed for the oxidation reaction of step i), or the gas effluent at the outlet of the top condenser of step iv) which is recycled to the oxidation reaction.

In the present invention, the term "(meth)acrylic" means "acrylic" or "methacrylic".

The term "azeotropic solvent" denotes any organic solvent which has the property of forming an azeotropic mixture with water.

The term "light" describing the by-product compounds denotes the compounds of which the boiling point is lower than that of (meth)acrylic acid, and by analogy, the term "heavy" denotes the compounds of which the boiling point is above that of (meth)acrylic acid.

The process according to the invention may also comprise other steps aimed at continuing the purification of the (meth)acrylic acid stream recovered in step vi).

According to one embodiment of the invention, the (meth)acrylic acid precursor is acrolein.

According to one embodiment of the invention, the acrolein is obtained by oxidation of propylene or by oxydehydrogenation of propane.

According to one embodiment of the invention, the (meth)acrylic acid precursor is methacrolein.

According to one embodiment of the invention, the methacrolein is obtained by oxidation of isobutylene and/or of tert-butanol.

According to one embodiment of the invention, the methacrolein is obtained from oxydehydrogenation of butane and/or isobutane.

According to one embodiment of the invention, the (meth)acrylic acid precursor is derived from glycerol, from 3-hydroxypropionic acid or from 2-hydroxypropanoic acid (lactic acid).

According to one preferred embodiment of the invention, the (meth)acrylic acid is acrylic acid and the acrylic acid precursor is acrolein obtained by catalytic oxidation of propylene. The gas reaction mixture comprises acrylic acid derived from propylene obtained according to a two-step oxidation process.

According to certain particular embodiments, the invention also exhibits one or, preferably, more of the advantageous characteristics listed below:

- the water condensation step is carried out using a single condenser for the two streams, or using a condenser for each of the two streams;
- the water condensation step is carried out at a temperature ranging from 15° C. to the temperature of the condenser at the top of the dehydration column;
- the step of condensing the water for the recycled gas effluent is preferably carried out at a temperature of between 40° C. and 60° C., more preferentially between 45° C. and 55° C.;
- the step of condensing the water for the air feed is preferably carried out at a temperature of between 15° C. and 25° C.;
- the condensed water is partly used to prepare aqueous solutions of polymerization inhibitor which are introduced into the dehydration column and/or into the finishing column, or their associated condensers;
- the condensed water is partly flushed and sent to the treatment of wastewater, or subjected to a thermal oxidation treatment.

The process according to the invention makes it possible to reduce the formation of a loop of water between the reaction and the dehydration column, the condensed water being advantageously used to prepare the aqueous solutions of polymerization inhibitor that are required for good operation of the process. The introduction of external water to prepare the inhibitor solutions is thus limited and the acrylic acid possibly present in the condensed water is recycled directly to the purification line, instead of being sent back to the reactor where it can be finally oxidized to carbon monoxide or dioxide.

The absence of external water makes it possible to adjust the operating conditions of the condenser at the top of the dehydration column by reducing its temperature, and consequently the acrylic acid losses are limited.

In addition, the performance levels of the (meth)acrylic acid precursor oxidation catalyst and its lifetime can be improved owing to a lower water content and lower organic impurity content in the oxidation reactor.

The process according to the invention may also comprise other steps or other characteristics provided that they do not negatively affect the effect provided by the present invention.

BRIEF DESCRIPTION OF DRAWINGS

Other characteristics and advantages of the invention will emerge more clearly on reading the detailed description which follows, with reference to appended FIGS. 1 to 5 which represent.

DETAILED DESCRIPTION OF THE INVENTION

The invention is based on the integration of at least one condenser into a (meth)acrylic acid production process including a solvent-free recovery/purification process of the prior art.

Figure 1:
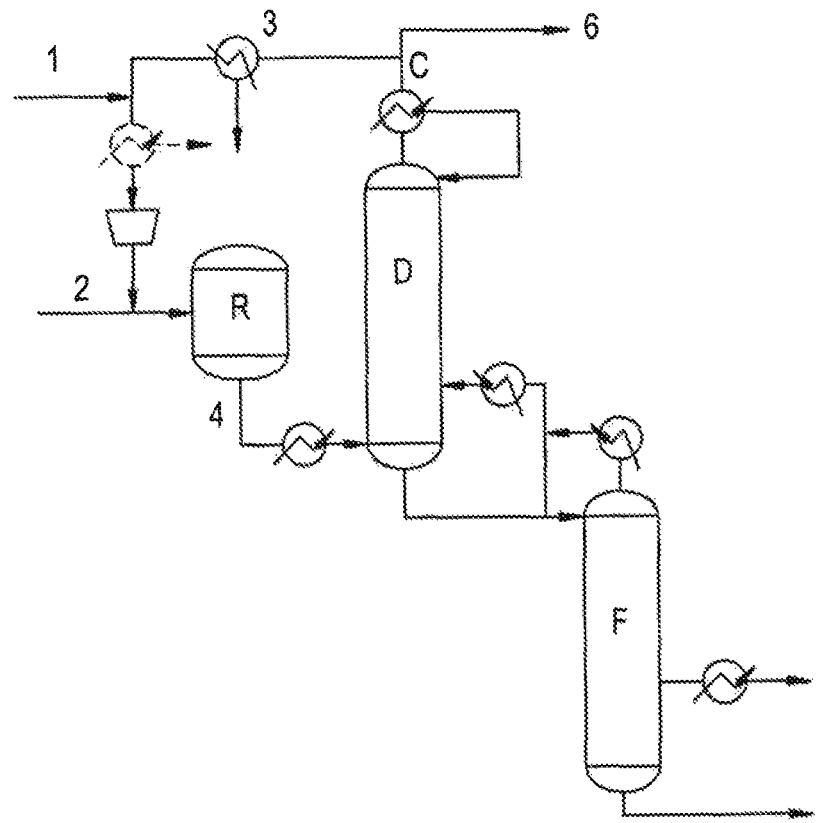
FIG. 1: facility suitable for implementing the process according to the invention.

Represented in FIG. 1 is a reactor R producing a gas reaction mixture 4 comprising (meth)acrylic acid obtained by gas-phase oxidation with air 1 of a (meth)acrylic acid precursor 2.

According to one embodiment, the reaction R is a set of 2 reactors in series or comprises at least 2 reaction zones in series, the first reactor or the first reaction zone being used for the synthesis of the (meth)acrylic acid precursor.

The gas reaction mixture comprising a water/(meth) acrylic acid weight ratio generally of between 0.3 and 2 can be pre-cooled before being sent to a first column, termed dehydration column D.

The dehydration column comprises, at the top, a top condenser C in which the light compounds and the water are partly condensed and sent back to the dehydration column in reflux form in order to absorb the acrylic acid. The gas effluent, comprising the non-condensable light compounds and water, is at least partly sent back to the reaction (stream 3) and the remainder (stream 6) is sent to a purification device, to a thermal oxidizer and/or a catalytic oxidizer, or is incinerated.

According to one embodiment, all of the stream from the top of the dehydration column is sent to the top condenser.

The dehydration column D operates, at least partially, as a distillation column, generally at atmospheric pressure or slightly above, to $1.5 \times 10^5$ Pa. Advantageously, the temperature in the upper part of the dehydration column is at least 40° C., preferably is between 40° C. and 80° C. The temperature of the stream at the bottom of the dehydration column preferably does not exceed 120° C.

No azeotropic solvent is added to the dehydration column.

The dehydration column generates a bottom stream comprising most of the (meth)acrylic acid with heavy by-products and a weight content of water of generally less than 10%, preferably less than 7%.

The stream at the bottom of the dehydration column is at least partly sent to the top of a second distillation column, termed finishing column F, or purification column.

The dehydration column and the finishing column may have various configurations, for example of the type of a column with random or structured packing or plate columns.

The temperature and the pressure in the purification column are not critical, and can be determined in accordance with the distillation methods known from the prior art. However, preferably, the purification column operates at a pressure below atmospheric pressure, making it possible to operate at relatively low temperatures, thus preventing polymerization of the unsaturated products present, and minimizing the formation of heavy by-products.

Advantageously, the purification column operates at a pressure ranging from 5 kPa to approximately 60 kPa, the temperature of the top stream advantageously being between 40° C. and approximately 90° C., and the temperature of the bottom stream being between 60° C. and 120° C.

The finishing column generates a top distillate comprising water and light by-products, which is condensed and then recycled to the bottom of the first column, and a bottom stream comprising acrylic acid enriched with heavy by-products, which is eliminated at the bottom so as to optionally be used for the production of acrylic esters.

The stream drawn off from the side of the finishing column F corresponds to a technical (meth)acrylic acid grade. It generally consists of (meth)acrylic acid with a purity greater than 98%, preferably greater than 99%. Preferably, it contains less than 1.5%, preferably less than 0.5%, more particularly less than 0.2% by weight of acetic acid, and less than 1%, preferably less than 0.5%, more particularly less than 0.3% by weight of water. This stream can further be subjected to purification by distillation, optionally coupled with a crystallization treatment.

According to the process of the invention, at least one condenser is placed on the gas effluent 3 which is recycled to the reactor R and/or on the air feed 1 in order to condense at least the water present in these streams.

It is possible to use a single condenser, or two condensers as represented in FIG. 1.

Refrigerated water or cold water is used to condense the gas. The temperature of the water can range from approximately 8° C. to approximately 45° C. depending on the condensation temperature. The condenser placed on the air feed is preferably cooled with refrigerated water at approximately 8° C. The condenser placed on the recycled gas effluent is preferably cooled with water at ambient temperature (about 25° C.).

The condenser may have various configurations, such as a tube bundle exchanger, a spiral exchanger, a finned tube exchanger, or a liquid contact condenser, etc.

The water condensation temperature can range from 15° C. to the temperature of the condenser at the top of the dehydration column which is generally below 65° C.

According to one embodiment, the temperature of the condenser placed at the level of the gas effluent 3 is between 40° C. and 60° C., preferably between 45° C. and 55° C.

According to one embodiment, the temperature of the condenser placed at the level of the air feed 1 is between 15° C. and 25° C.

According to one embodiment, the condensed air from the air feed, which is free of organic impurities, is advantageously at least partly recycled to the water cooling towers.

According to one embodiment, the condensed water is partly used to prepare aqueous solutions of polymerization inhibitor which can be introduced into the facility at various places.

The polymerization inhibitors are chosen from compounds which inhibit the (meth)acrylic acid polymerization reaction. As examples of usable compounds, mention may be made of phenothiazine, hydroquinone, 2,2,6,6-tetramethyl-1-piperidinyloxy (Tempo) or one of the derivatives thereof such as 4-hydroxy Tempo, soluble copper salts, and soluble manganese salts, alone or as a mixture The aqueous solutions of polymerization inhibitor are added in a sufficient amount known to those skilled in the art in order to prevent or reduce the (meth)acrylic acid polymerization in the facility, in particular in the stream at the top of the dehydration column at the level of the top condenser, or in the stream at the top of the finishing column, at the level of the condenser associated with said column, or in the stream of purified product drawn off from the side of the finishing column, optionally after condensation in the case where the stream drawn off is in gas form.

The process according to the invention results in the production of (meth)acrylic acid with an improved yield compared to the prior art processes. This is because the use of a condenser on the gas effluent recycled to the reaction and/or to the air feed has made it possible to reduce the acrylic acid loss by more than 50% compared to a process which does not comprise a condensation step in order to limit the entry of water into the reactor. Moreover, in addition to the reduction in the acrylic acid losses, it has been possible to reduce the temperature of the top condenser by about 2 to 4° C., which has an additional advantage in terms of energy.

The invention will now be illustrated by the following examples, the objective of which is not to limit the scope of the invention, defined by the claims.

EXPERIMENTAL SECTION

Example 1 (Reference)

Figure 2:
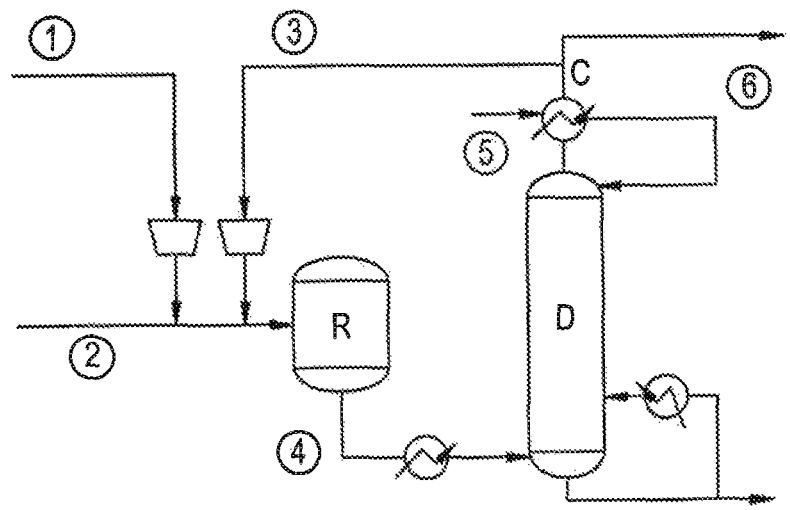
FIG. 2: diagram of the prior art.

With reference to FIG. 2, representing a prior art process for producing acrylic acid (AA), a reactor is fed with a stream 2 of polypropylene and a stream 1 of air.

At the outlet of the reactor, a gas reaction mixture comprising the acrylic acid produced is sent, after cooling in an exchanger, to a dehydration column D surmounted by a top condenser C. A stream 5 of an aqueous solution of polymerization inhibitor is introduced at the level of the top condenser C. A part of the gas effluent 3 is recycled to the reactor, and a part of the gas effluent 6 is sent to an incinerator.

A simulation using the Aspen software was used to characterize the acrylic acid loss in this type of facility.

The results are presented in Table 1 below:

TABLE 1

| AA produced by the reaction, kg/h | 11805 |
| AA lost at the top of the condenser C, kg/h | 206 |
| Loss of AA at the top of C, % | 1.74 |
| Temperature of the top condenser C, ° C. | 60.9 |
| Water at inlet of the reactor R, % | 6.58 |
| Water at outlet of the reactor R, kg/h | 6660 |
| AA at outlet of the reactor R, kg/h | 11871 |
| AA/water ratio at outlet of the reactor R | 1.78 |

Example 2 (According to the Invention)

Figure 3:
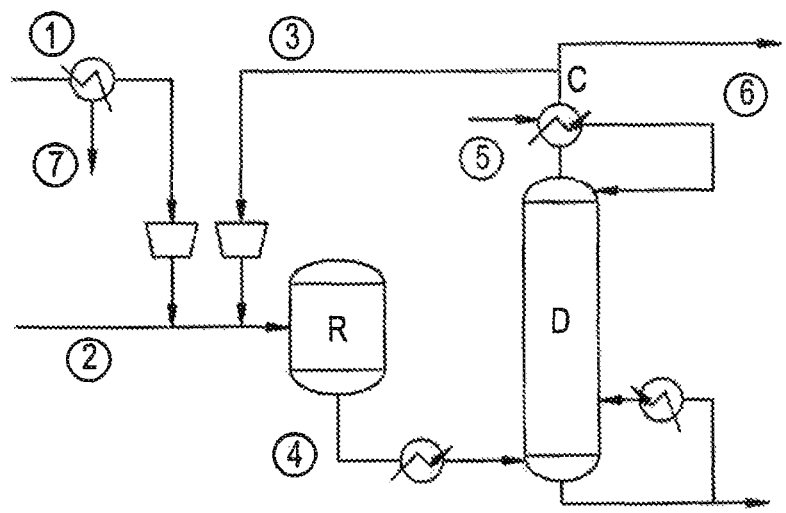
FIG. 3: diagram illustrating a first embodiment of the invention.

FIG. 3 represents a first embodiment of the invention. With respect to FIG. 2, a condenser/cooler was placed on the stream of feed air 1. The stream of water 7 condensed at 15° C. can be recycled to the cooling towers.

The Aspen simulation results are collated in Table 2 below.

By eliminating the moisture content present in the air which feeds the reactor, it is noted that the acrylic acid losses at the top of the condenser are reduced by close to 50% compared with the case in Example 1.

TABLE 2

| AA produced by the reaction, kg/h | 11813 |
| AA lost at the top of the condenser C, kg/h | 112 |
| Loss of AA at the top of C, % | 0.95 |
| Temperature of the top condenser C, ° C. | 58.8 |
| Water at inlet of the reactor R, % | 5.05 |
| Water at outlet of the reactor R, kg/h | 6002 |
| AA at outlet of the reactor R, kg/h | 11853 |
| AA/water ratio at outlet of the reactor R | 1.97 |

Example 3 (According to the Invention)

Figure 4:
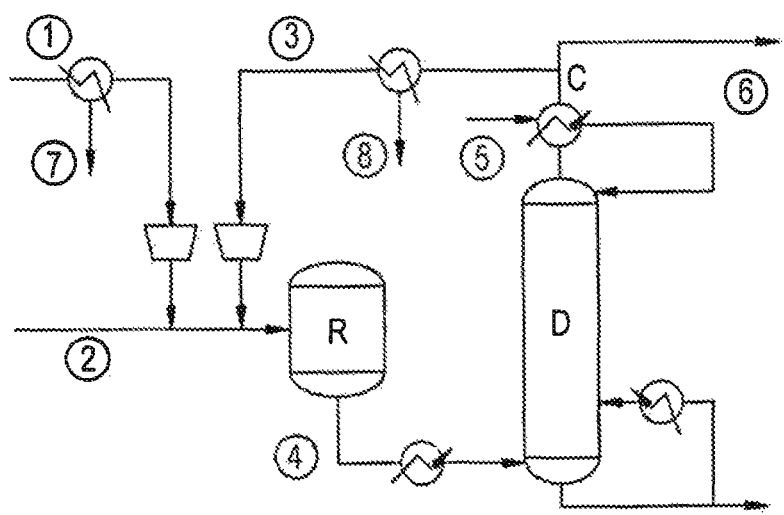
FIG. 4: diagram illustrating a second embodiment of the invention.

FIG. 4 represents a second embodiment of the invention. With respect to FIG. 2, a condenser/cooler was placed on the stream of feed air 1, and a condenser was placed on the effluent 3 recycled to the reactor. The condensed stream of water 7 originating from the moisture content of the air can be recycled to the cooling towers. The condensate 8 is eliminated from the process.

According to this configuration, two Aspen simulations were performed, according to Table 3.

TABLE 3

|  | Test 1 | Test 2 |
| --- | --- | --- |
| AA produced by the reaction, kg/h | 11818 | 11820 |
| AA lost at the top of the condenser C, kg/h | 73 | 59 |
| Loss of AA at the top of C, % | 0.69 | 0.58 |
| Temperature of the condenser of the recycled effluent, 0° C. | 53 | 50 |
| Condensate 8 originating from the recycled effluent, kg/h | 398.4 | 562.9 |
| Recycled condensate, kg/h | 0 | 0 |
| Loss of AA in the condensate, kg/h | 8.3 | 9.5 |
| Temperature of the top condenser C, ° C. | 57.4 | 56.7 |
| Water at inlet of the reactor R, % | 4.14 | 3.75 |
| Water at outlet of the reactor R, kg/h | 5602 | 5430 |
| AA at outlet of the reactor R, kg/h | 11837 | 11833 |
| AA/water ratio at outlet of the reactor R | 2.11 | 2.18 |

In this table, the percentage of AA loss at the top of the condenser C takes into account the loss of AA present in the condensate 8.

Under these conditions, even though the condensed water stream from the recycled gas effluent is eliminated, the overall loss of AA remains lower than that of Reference Example 1. Furthermore, the condenser C can operate at a lower temperature.

Example 4 (According to the Invention)

Figure 5:
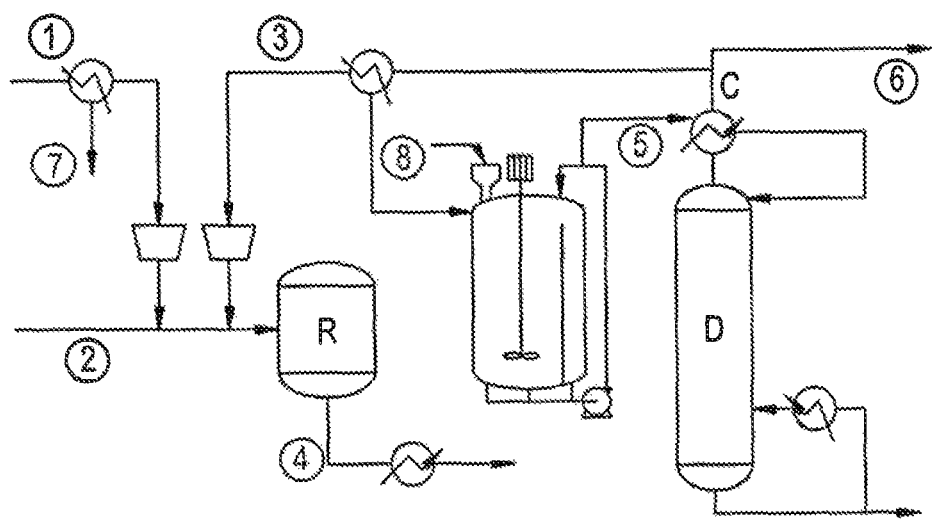
FIG. 5: diagram illustrating a third embodiment of the invention.

FIG. 5 represents a third embodiment of the invention. With respect to FIG. 4, the condensate 8 is introduced into a stirred tank, into which at least one polymerization inhibitor is introduced, and the aqueous solution of inhibitor 5 thus prepared in situ can be directly introduced at the level of the condenser C.

The Aspen simulation results are collated in Table 4 below:

TABLE 4

| | |
|---|---|
| AA produced by the reaction, kg/h | 11818 |
| AA lost at the top of the condenser C, kg/h | 77 |
| Loss of AA at the top of C, % | 0.65 |
| Temperature of the condenser of the recycled effluent, ° C. | 53 |
| Condensate 8 originating from the recycled effluent, kg/h | 0 |
| Recycled condensate, kg/h | 395 |
| Loss of AA in the condensate, kg/h | 0 |
| Temperature of the top condenser C, ° C. | 57.3 |
| Water at inlet of the reactor R, % | 4.12 |
| Water at outlet of the reactor R, kg/h | 5596 |
| AA at outlet of the reactor R, kg/h | 11838 |
| AA/water ratio at outlet of the reactor R | 11818 |

This embodiment not only makes it possible to reduce the AA loss, but also does not require any external clean water to prepare the aqueous solution inhibitors.

The invention claimed is:

1. A process for production of (meth)acrylic acid, comprising at least the following steps:
   i) subjecting at least one (meth)acrylic acid precursor to gas-phase oxidation in the presence of an air feed so as to form a gas reaction mixture comprising (meth)acrylic acid;
   ii) cooling the gas reaction mixture;
   iii) subjecting the gas reaction mixture to dehydration without using azeotropic solvent in a dehydration column, resulting in a first top gas stream and in a first bottom stream;
   iv) at least partly subjecting the first top gas stream distilled at the top of the dehydration column to condensation in a top condenser to form condensate, the condensate being returned to the dehydration column in reflux form to absorb acrylic acid, and at least partly returning gas effluent to the oxidation reaction, and subjecting a remainder to thermal and/or catalytic oxidation;
   v) at least partly subjecting the first bottom stream from the bottom of the dehydration column to distillation in a finishing column, resulting in a second top stream, and in a second bottom stream containing heavy compounds;
   vi) recovering (meth)acrylic acid stream by drawing off (meth)acrylic acid from a side of the finishing column; and further applying a water condensation step to at least one of two streams selected from the group consisting of: the air feed for the oxidation reaction of step i), and the gas effluent at an outlet of the top condenser of step iv) which is recycled to the oxidation reaction.

2. The process according to claim 1, wherein the water condensation step is carried out using a single condenser for the two streams or using a condenser for each of the two streams.

3. The process according to claim 1, wherein the water condensation step is carried out at a temperature ranging from 15° C. to the temperature of the condenser at the top of the dehydration column.

4. The process according to claim 1 wherein the step of condensing the water for the recycled gas effluent is carried out at a temperature of between 40° C. and 60° C.

5. The process according to claim 1 wherein the step of condensing the water for the air feed is carried out at a temperature of between 15° C. and 25° C.

6. The process according to claim 1 wherein the condensed water from the air feed is at least partly recycled to water cooling towers.

7. The process according to claim 1 wherein the condensed water is partly used to prepare aqueous solutions of polymerization inhibitors.

8. The process according to claim 1 wherein the condensed water is partly flushed and sent to the treatment of wastewater, or subjected to a thermal oxidation treatment.

9. The process according to claim 1 wherein the (meth)acrylic acid precursor is acrolein, obtained by oxidation of propylene or by oxydehydrogenation of propane.

10. The process according to claim 1 wherein the (meth)acrylic acid precursor is methacrolein obtained by oxidation of isobutylene and/or of tert-butanol or from oxydehydrogenation of butane and/or isobutane.

11. The process according to claim 1 wherein the (meth)acrylic acid precursor is derived from glycerol, from 3-hydroxypropionic acid or from 2-hydroxypropanoic acid.

12. The process according to claim 1 wherein the (meth)acrylic acid is acrylic acid and the acrylic acid precursor is acrolein obtained by catalytic oxidation of propylene.

* * * * *